US009975868B2

(12) United States Patent
Ye

(10) Patent No.: US 9,975,868 B2
(45) Date of Patent: *May 22, 2018

(54) 7,8-DIHYDOXYFLAVONE AND 7,8-SUBSTITUTED FLAVONE DERIVATIVES, COMPOSITIONS, AND METHODS RELATED THERETO

(71) Applicant: EMORY UNIVERSITY, Atlanta, GA (US)

(72) Inventor: Keqiang Ye, Lilburn, GA (US)

(73) Assignee: Emory University, Atlanta, GA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/593,654

(22) Filed: May 12, 2017

(65) Prior Publication Data

US 2017/0305876 A1 Oct. 26, 2017

Related U.S. Application Data

(62) Division of application No. 14/437,232, filed as application No. PCT/US2013/067972 on Nov. 1, 2013, now Pat. No. 9,682,948.

(60) Provisional application No. 61/845,399, filed on Jul. 12, 2013, provisional application No. 61/722,339, filed on Nov. 5, 2012.

(51) Int. Cl.
| | |
|---|---|
| C07D 311/30 | (2006.01) |
| C07D 311/28 | (2006.01) |
| A61K 45/06 | (2006.01) |
| A61K 31/352 | (2006.01) |
| C07D 311/36 | (2006.01) |
| C07D 311/38 | (2006.01) |

(52) U.S. Cl.
CPC .......... *C07D 311/30* (2013.01); *A61K 31/352* (2013.01); *A61K 45/06* (2013.01); *C07D 311/28* (2013.01); *C07D 311/36* (2013.01); *C07D 311/38* (2013.01)

(58) Field of Classification Search
CPC .................................................. C07D 311/30
USPC ....................................................... 514/456
See application file for complete search history.

(56) References Cited

U.S. PATENT DOCUMENTS

| | | | |
|---|---|---|---|
| 2002/0128494 | A1 | 9/2002 | Mihokne et al. |
| 2002/0160983 | A1 | 10/2002 | Bargiotti et al. |
| 2003/0125264 | A1 | 7/2003 | Malik et al. |
| 2004/0063665 | A1 | 4/2004 | Bargiotti et al. |
| 2010/0022587 | A1 | 1/2010 | Krejci et al. |
| 2010/0179210 | A1 | 7/2010 | Sivakumar et al. |

FOREIGN PATENT DOCUMENTS

| | | |
|---|---|---|
| CN | 101591319 | 12/2009 |
| CN | 102143744 | 8/2011 |
| WO | 2010/011836 | 1/2010 |
| WO | 2010/107866 | 9/2010 |
| WO | 2011/156479 | 12/2011 |

OTHER PUBLICATIONS

EP13851584.6, "Extended European Search Report", dated Feb. 18, 2016, 7 pages.
Communication pursuant to Article 94(3) EPC for European Application No. 13851584.6 dated Feb. 15, 2017; 4 pages.
Examination Report No. 1 for Australian Application No. 2013337742 dated Mar. 3, 2017; 3 pages.
International Search Report and Written Opinion for Application No. PCT/US2013/067972 dated Feb. 11, 2014.
Office Action for Chinese Patent Application No. 201380062367.X dated Apr. 12, 2016 along with an English translation.
Office Action for Chinese Patent Application No. 201380062367.X dated Nov. 25, 2016 along with an English translation.
Arancio et al., "Neurotrophins, synaptic plasticity and dementia", 2007, Current Opinion in Neurobiology, 17 (3): 325-30.
Baker, "The Formation of Chromones", Journal of the Chemical Society, Transactions (1925), 125, 2349-58.
Chen et al., "Interaction of flavones and their bromoacetyl derivatives with NAD(P)H:quinone acceptor oxidoreductase.", Molecular Pharmacology, vol. 47, No. 2, Feb. 1995, pp. 419-424.
Chiruta et al., "Chemical Modification of the Multitarget Neuroprotective Compound Fisetin", 2012, Journal of Medicinal Chemistry, 55, 378-89.
Devi & Ohno, "7,8-dihydroxyflavone, a small-molecule TrkB agonist, reverses memory deficits and BACE1 elevation in a mouse model of Alzheimer's disease", Neuropsychopharmacology, 2012, 37(2):434-44.
Dwivedi,"Brain-derived neurotrophic factor: role in depression and suicide", Neutopsychiatric Disease and Treatment, 2009, 5: 433-49.
Jang et al., "A selective TrkB agonist with potent neurotrophic activities by 7,8-dihydroxyflavone", Proceedings of the National Academy of Sciences, vol. 107, No. 6, Feb. 9, 2010, pp. 2687-2692.
Jiao et al., "A Robust Boosting Regression Tree with Applications in Quantitative Structure—Activity Relationship Studies of Organic Compounds", J. Chem. Inf. Model. 2011, 51, 816-828 and supporting information pp. 1-9.

(Continued)

*Primary Examiner* — Taofiq A Solola
(74) *Attorney, Agent, or Firm* — Kilpatrick Townsend & Stockton LLP

(57) ABSTRACT

In certain embodiments, the disclosure relates to 7,8-dihydoxyflavone and 7,8-substituted flavone derivatives, such as those described by formula provided herein, pharmaceutical compositions, and methods related thereto. In certain embodiments, the disclosure relates to methods of treating or preventing diseases or conditions related to BDNF and TrkB activity, such as psychiatric disorders, depression, post-traumatic stress disorder, and autism spectrum disorders, stroke, Rett syndrome, Parkinson's disease, and Alzheimer's disease by administering effective amounts of pharmaceutical compositions comprising compounds disclosed herein to a subject in need thereof. In certain embodiments, it is contemplated that the 7,8-substituted flavone derivatives disclosed herein are prodrugs of 7,8-dihydoxyflavone and analogs.

14 Claims, 4 Drawing Sheets

(56) References Cited

OTHER PUBLICATIONS

Kaplan et al., "A DRD4/BDNF gene—gene interaction associated with maximum BMI in women with bulimia nervosa", International Journal of Eating Disorders, 2008 41 (1): 22-8.

Liederer &, Borchardt, "Enzymes involved in the bioconversion of ester-based prodrugs", J Pharm Sci, 2006, 95(6):1177-95.

Liu et al., "A synthetic 7,8-dihydroxyflavone derivative promotes neurogenesis and exhibits potent antidepressant effect", J Med Chem, 2010, 53 (23), pp. 8274-8286.

Maina et al., "Serum levels of brain-derived neurotrophic factor in drug-naïve obsessive-compulsive patients: a case-control study", Journal of Affective Disorders, 2010, 122(1-2):174-8.

Mehesh et al., "Selective methylation of chelated hydroxyl groups" CA 51: 17099 (1957).

Mercader et al, "Blood Levels of Brain-Derived Neurotrophic Factor Correlate with Several Psychopathological Symptoms in Anorexia Nervosa Patients", Neuropsychobiology, 2007, 56 (4): 185-90.

Seema et al., "Characterization of Protein Transacetylase From Human Placenta as a Signaling Molecule Calreticulin Using Polyphenolic Peracetates as the Acetyl Group Donors", Cell Biochemistry and Biophysics, vol. 47, 2007, pp. 53-64.

Sousa et al., "Flavone—Nitrogen Heterocycle Conjugate Formation by 1,3-Dipolar Cycloadditions", 2012, European Journal of Organic Chemistry, 1, 132-43.

Xiu et al., "Decreased serum BDNF levels in chronic institutionalized schizophrenia on long-term treatment with typical and atypical antipsychotics", Progress in Neuro-Psychopharmacology and Biological Psychiatry, 2009, 33(8):1508-12.

Yushchenko et al., "Synthesis and fluorescence properties of 2-aryl-3-hydroxyquinolones, a new class of dyes displaying dual fluorescence," 2006, Tetrahedron Letters, 47, 905-8.

Zajac et al., "Wheel running and environmental enrichment differentially modify exon-specific BDNF expression in the hippocampus of wild-type and pre-motor symptomatic male and female Huntington's disease mice", 2010, Hippocampus 20 (5): 621-36.

Zeev et al., "The common BDNF polymorphism may be a modifier of disease severity in Rett syndrome", Neurology, 2009, 72 (14): 1242-7.

Zeng et al., "Epigenetic enhancement of BDNF signaling rescues synaptic plasticity in aging", J. Neuroscience, 2011, 31(49):17800-17810 (Retracted).

Zuccato et al., "Brain-derived neurotrophic factor in neurodegenerative diseases", Nature Reviews Neurology, 2009, 5(6):311-22.

* Notice of Allowance issued in U.S. Appl. No. 14/437,232 dated Feb. 24, 2017.
* Final Office Action issued in U.S. Appl. No. 14/437,232 dated Sep. 2, 2016.
* Non-Final Office Action issued in U.S. Appl. No. 14/437,232 dated Apr. 13, 2016.

Bundgaard, "Novel chemical approaches in prodrug design," Drugs of the Future, 1991, vol. 16, No. 5, pp. 443-458.

Larsen et al., "Design and application of prodrugs," Textbook of Drug Design and Discovery, 2002, Chapter 14, pp. 460-514.

Murthy et al., "Synthesis of New Flavanoid Derivatives as Liquid Crystals Part-1," Indian Journal of Heterocyclic Chemistry, vol. 1, 1991, pp. 91-94.

Office Action issued in Japanese Application No. 2015-540801 dated Aug. 15, 2017 along with an English translation.

Office Action for Chinese Application No. 201380062367.X dated May 10, 2017 along with an English translation.

7,8-DIHYDOXYFLAVONE AND 7,8-SUBSTITUTED FLAVONE DERIVATIVES, COMPOSITIONS, AND METHODS RELATED THERETO

CROSS REFERENCE TO RELATED APPLICATIONS

This application is a division of U.S. application Ser. No. 14/437,232, filed on Apr. 21, 2015, which is a U.S. national stage application under 35 U.S.C. § 371 of PCT/US2013/067972, filed on Nov. 1, 2013, which claims the benefit of U.S. Provisional Application No. 61/722,339, filed Nov. 5, 2012, and U.S. Provisional Application No. 61/845,399, filed Jul. 12, 2013. The above-listed applications are incorporated herein by reference in their entireties.

STATEMENT REGARDING FEDERALLY FUNDED RESEARCH

This invention was made with government support under grant number R01DC010204 awarded by the National Institutes of Health. The government has certain rights in the invention.

FIELD

In certain embodiments, the disclosure relates to 7,8-dihydoxyflavone and 7,8-substituted flavone derivatives, such as those described by formula provided herein, pharmaceutical compositions, and methods related thereto. In certain embodiments, the disclosure relates to methods of treating or preventing diseases or conditions related to BDNF and TrkB activity, such as psychiatric disorders, depression, post-traumatic stress disorder, and autism spectrum disorders, stroke, Rett syndrome, Parkinson's disease, and Alzheimer's disease by administering effective amounts of pharmaceutical compositions comprising compounds disclosed herein to a subject in need thereof. In certain embodiments, it is contemplated that the 7,8-substituted flavone derivatives disclosed herein are prodrugs of 7,8-dihydoxyflavone and analogs.

BACKGROUND

Neurotrophins are growth factors regulate the development and maintenance of the peripheral and the central nervous system. Brain-derived neutrotrophic factor (BDNF) is a member of the neurotrophin family, which includes nerve growth factor (NGF), NT-3 and NT-4/5. BDNF binding to its cognate receptor, TrkB, triggers its dimerization through conformational changes and autophosphorylation of tyrosine residues, resulting in activation of the three major signaling pathways—mitogen-activated protein (MAPK), phosphatidylinositol 3-kinase (PI3K) and phospholipase C-γ1 (PLC-γ1). Various studies have shown links between BDNF and TrkB to conditions such as depression, schizophrenia, obsessive-compulsive disorder, Alzheimer's disease, Huntington's disease, Rett syndrome, and dementia, as well as anorexia nervosa and bulimia nervosa. See Dwivedi, Neutopsychiatric Disease and Treatment, 2009, 5: 433-49; Xiu et al., Progress in Neuro-Psychopharmacology and Biological Psychiatry, 2009, 33(8):1508-12; Maina et al., Journal of Affective Disorders, 2010, 122(1-2):174-8; Zuccato et al., Nature Reviews Neurology, 2009, 5(6):311-22; Zajac et al., 2010, Hippocampus 20 (5): 621-36; Zeev et al., Neurology, 2009, 72 (14): 1242-7; Arancio et al., 2007, Current Opinion in Neurobiology, 17 (3): 325-30; Mercader et al, Neuropsychobiology, 2007, 56 (4): 185-90; Kaplan et al., International Journal of Eating Disorders, 2008 41 (1): 22-8. Epigenetic enhancement of BDNF signaling rescues synaptic plasticity in aging. See Zeng et al., J. Neuroscience, 2011, 31(49):17800-17810. 7,8-dihydroxyflavone reverses memory deficits and BACE1 elevation in a mouse model of Alzheimer's disease. See Devi & Ohno, Neuropsychopharmacology, 2012, 37(2):434-44.

It has been reported that certain 7,8-dihydroxyflavone derivatives promote neurogenesis and exhibits potent antidepressant effects. See Liu et al., J Med Chem, 2010, 53 (23), pp 8274-8286. See also WO/2010/011836, WO/2010/107866, and WO 2011/156479. As 7,8-dihydroxyflavone derivatives are catechol and phenyl containing compounds, they are prone to be cleared in the circulatory system following oxidation, glucuronidation, sulfation or methylation. Thus, there is a need to identify improved flavone derivatives with improved pharmacokinetic properties.

The health benefits of flavonoid compounds have been reported in a number of references, including neuroprotective and anti-cancer properties. See Chiruta et al., 2012, Journal of Medicinal Chemistry, 55, 378-89; Sousa et al., 2012, European Journal of Organic Chemistry, 1, 132-43; Sivakumar et al., PCT Appl. No. US 2010/0179210. Derivatives of 3-hydroxyquinolone compounds have also been previously synthesized with reports of their fluorescence and biological activities disclosed. See Yushchenko et al., 2006, Tetrahedron Letters, 47, 905-8; Krejci et al., PCT Appl. No. US 2010/0022587.

A prodrug is a pharmacological substance that is administered and is subsequently converted to an active pharmacological agent through normal metabolic processes. Enzymes are involved in the bioconversion of ester-based prodrugs. See Liederer &, Borchardt, J Pharm Sci, 2006, 95(6):1177-95.

The references cited hereby are not an admission of prior art.

SUMMARY

In certain embodiments, the disclosure relates to 7,8-dihydoxyflavone and 7,8-substituted flavone derivatives, such as those described by formula provided herein, pharmaceutical compositions, and methods related thereto. In certain embodiments, the disclosure relates to methods of treating or preventing diseases or conditions related to BDNF and TrkB activity, such as psychiatric disorders, depression, post-traumatic stress disorder, and autism spectrum disorders, stroke, Rett syndrome, Parkinson's disease, and Alzheimer's disease by administering effective amounts of pharmaceutical compositions comprising compounds disclosed herein to a subject in need thereof. In certain embodiments, it is contemplated that the 7,8-substituted flavone derivatives disclosed herein are prodrugs of 7,8-dihydoxyflavone and analogs.

In certain embodiments, the disclosure related to a compound comprising Formula I:

Formula I

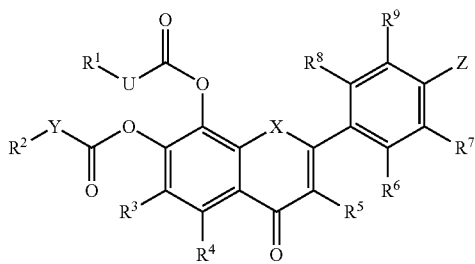

or salts thereof wherein
X is O, S, or NH;
U and Y are each O, S, NH, Nalkyl, or $CH_2$;
Z is hydrogen, amino, diaminoalkyl, or heterocyclyl such as pyrrolidinyl optionally substituted with one or more, the same or different, $R^{15}$;
$R^1$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^1$ is optionally substituted with one or more, the same or different, $R^{15}$;
$R^2$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^2$ is optionally substituted with one or more, the same or different, $R^{15}$;
$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;
$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and
$R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure contemplates compositions comprising compounds disclosed herein in greater than 90%, 95%, or 98% purity by weight.

In certain embodiments, the disclosure relates to pharmaceutical compositions comprising compounds disclosed herein and a pharmaceutically acceptable excipient. In certain embodiments, the pharmaceutical composition is in the form of a tablet, capsule, pill, or solution for injection. In certain embodiments, it is contemplated that the pharmaceutical composition comprises greater than 0.1%, 1%, 5%, 10%, 20%, 30%, 40%, or 50% of a compound disclosed herein by weight.

In certain embodiments, the disclosure relates to methods of preventing or treating a BDNF and TrkB related disease or condition comprising the administering an effective amount of a pharmaceutical composition disclosed herein, to a subject in need thereof. In some embodiments, the subject is diagnosed with, exhibiting symptoms of, or at risk of the disease or condition. In some embodiments, the disease or condition is depression, schizophrenia, obsessive-compulsive disorder, anorexia nervosa, bulimia nervosa, anxiety, amytrophic later sclerosis, Autism spectrum disorders, Alzheimer's disease, Huntington's disease, Rett's syndrome, epilepsy, Parkinson's disease, dementia, diabetic neuropathy, peripheral neuropathy, obesity, peripheral nerve injury, pain, or stroke.

In certain embodiments, the disease is depression and the pharmaceutical composition is administered in combination with an anti-depressant such as a selective serotonin reuptake inhibitor such as citalopram, escitalopram, fluoxetine, fluvoxamine, paroxetine, sertraline, or vilazodone, a serotonin-norepinephrine reuptake inhibitor such as desvenlafaxine, duloxetine, milnacipran, venlafaxine, a noradrenergic and specific serotonergic antidepressant such as mianserin and mirtazapine, a norepinephrine reuptake inhibitor such as atomoxetine, mazindol, reboxetine, viloxazine, a norepinephrine-dopamine reuptake inhibitor such as bupropion, a selective serotonin reuptake enhancer such as tianeptine and aminoptine, a norepinephrine-dopamine disinhibitor such as agomelatine, a tricyclic antidepressant such as amitriptyline, clomipramine, doxepin, imipramine, trimipramine, desipramine, nortriptyline, protriptyline, a monoamine oxidase inhibitor such as isocarboxazid, moclobemide, phenelzine, selegiline, tranylcypromine.

In certain embodiments, the disclosure contemplates treatment or prevention of dementia, Alzheimer's, or Parkinson's disease by administering 7,8-dihydroxyflavone and derivatives disclosed herein in combination with a dementia agent such as levodopa, carbidopa, pramipexole, rotigotine, ropinirole, artane, cogentin, amantadine, deprenyl, donepezil, galantamine, memantine, rivastigmine, tacrine, and vitamin E. In certain embodiments, the disclosure contemplates pharmaceutical agents comprising combinations of these therapeutics.

In some embodiments, the disclosure relates to the use of a compound disclosed herein in the production of a medicament for the treatment or prevention of a BDNF and TrkB related disease or condition.

In certain embodiments, the disclosure contemplates method of producing compounds disclosed herein comprising mixing starting materials with 7,8-dihydroxyflavone or derivatives under conditions such that the compounds are formed.

DETAILED DISCUSSION

Terms

Figure 1:
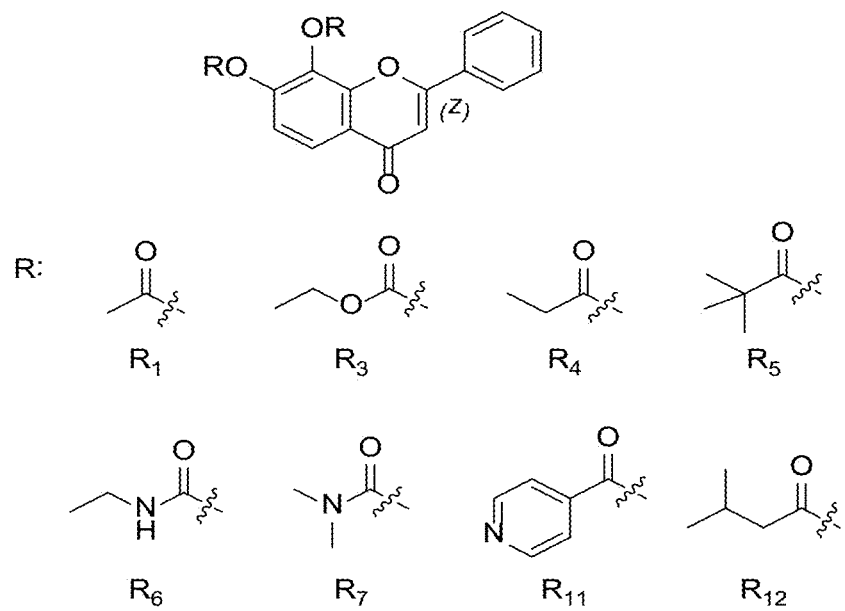
FIG. 1 illustrates various embodiments of the disclosure.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Embodiments of the present disclosure will employ, unless otherwise indicated, techniques of synthetic organic chemistry, biochemistry, biology, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein a "flavone" refers to any compound comprising a 2-phenyl-4H-chromen-4-one ring system.

As used herein, "alkyl" means a noncyclic straight chain or branched, unsaturated or saturated hydrocarbon such as those containing from 1 to 10 carbon atoms, typically 1 to 6 carbon atoms. Within any embodiments, herein alkyl may refer to an alkyl with 1 to 6 carbons ($C_{1-6}$alkyl). Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH$_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkyloxycarbonyl" refers to an alkyl as defined above attached through a carboxy bridge (i.e., —(C=O)Oalkyl.

"Alkylcarbamoyl" refers to an alkyl as defined above attached through a carbonyl bridge (i.e., —(C=O)NHalkyl).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above attached through a sulfamoyl bridge (i.e., —S(=O)$_2$NHalkyl), and an "Arylsulfonamide" refers to an alkyl attached through a sulfamoyl bridge (i.e., (i.e., —S(=O)$_2$NHaryl).

"Alkylsulfinyl" refers to an alkyl as defined attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, aryl alkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulphur atom or replacing an amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Compounds

In certain embodiments, the disclosure relates to compounds Formula I:

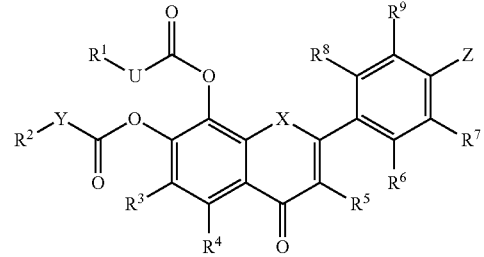

Formula I or salts thereof wherein

X is O, S, or NH;

U and Y are each O, S, NH, Nalkyl, or CH$_2$;

Z is hydrogen, amino, diaminoalkyl, or heterocyclyl such as pyrrolidinyl optionally substituted with one or more, the same or different, $R^{15}$;

$R^1$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, arylsulfonyl, carbocyclyl, or aryl, wherein $R^1$ is optionally substituted with one or more, the same or different, $R^{15}$;

$R^2$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^2$ is optionally substituted with one or more, the same or different, $R^{15}$;

$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^3$, $R^4$, $R^6$, $R^7$, $R^8$, and $R^9$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $-O(C=O)-U-R^1$ and/or $-O(C=O)-Y-R^2$ are an amino acid ester or polypeptide ester.

In certain embodiments, X is O.

In certain embodiments, $R^7$ and $R^9$ are a halogen, one of or both.

In certain embodiments, Z is hydrogen or a nonaromatic heterocyclyl bond to the phenyl ring through a nitrogen heteroatom.

In certain embodiments, U and Y are oxygen.

In certain embodiments, U and Y are NH or Nalkyl; and $R^1$ and $R^2$ are alkyl.

In certain embodiments, $R^3$, $R^4$, $R^5$, $R^6$, $R^7$, $R^8$, and $R^9$ are hydrogen.

In certain embodiments, the compound is selected from:
4-oxo-2-phenyl-4H-chromene-7,8-diyl bis(methylcarbamate);
4-oxo-2-phenyl-4H-chromene-7,8-diyl dipropionate;
4-oxo-2-phenyl-4H-chromene-7,8-diyl bis(2,2-dimethylpropanoate);
diethyl (4-oxo-2-phenyl-4H-chromene-7,8-diyl) dicarbonate;
4-oxo-2-phenyl-4H-chromene-7,8-diyl bis(ethylcarbamate);
4-oxo-2-phenyl-4H-chromene-7,8-diyl bis(dimethylcarbamate); and
4-oxo-2-phenyl-4H-chromene-7,8-diylbis(3-methylbutanoate) or salts thereof.

In certain embodiments, the disclosure relates to compounds Formula II:

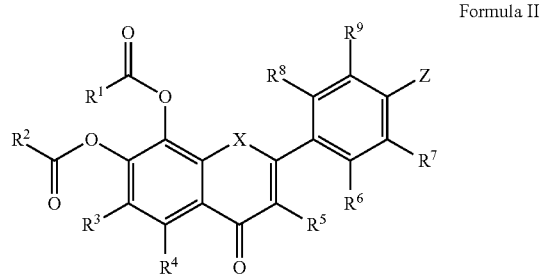

Formula II or salts thereof wherein

X is O, S, or NH;

Z is hydrogen, amino, diaminoalkyl, or heterocyclyl such as pyrrolidinyl optionally substituted with one or more, the same or different, $R^{15}$;

$R^1$ and $R^2$ are a heterocyclyl optionally substituted with one or more, the same or different, $R^{15}$; or $R^1$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^1$ is optionally substituted with one or more, the same or different, $R^{15}$;

$R^2$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^2$ is optionally substituted with one or more, the same or different, $R^{15}$;

$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $-O(C=O)-R^1$ and/or $-O(C=O)-R^2$ are an amino acid ester or polypeptide ester.

In certain embodiments, X is O.

In certain embodiments, $R^7$ and $R^9$ are a halogen, one of or both.

In certain embodiments, Z is hydrogen or a nonaromatic heterocyclyl bond to the phenyl ring through a nitrogen heteroatom.

In certain embodiments, $R^1$ and $R^2$ are pyridinyl.

In certain embodiments, $R^3$, $R^4$, $R^5$, $R^6$, $R^7$, $R^8$, and $R^9$ are hydrogen.

In certain embodiments, the compound is 4-oxo-2-phenyl-4H-chromene-7,8-diyl diisonicotinate.

In certain embodiments, the disclosure relates to compounds Formula III:

Formula III

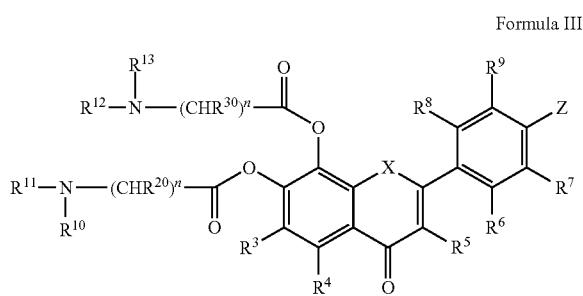

or salts thereof wherein
n are each individually and independently 1 to 22;
X is O, S, or NH;
Z is hydrogen, amino, diaminoalkyl, or heterocyclyl such as pyrrolidinyl optionally substituted with one or more, the same or different, $R^{15}$;
$R^{10}$, $R^{11}$, $R^{12}$, and $R^{13}$ are each individually and independently hydrogen, alkyl, halogen, nitro, cyano, hydroxy, amino, mercapto, formyl, carboxy, carbamoyl, alkoxy, alkylthio, alkyl amino, (alkyl)$_2$amino, alkylsulfinyl, alkyl sulfonyl, aryl sulfonyl, carbocyclyl, aryl, or heterocyclyl, wherein $R^{10}$, $r^{11}$, $R^{12}$, and $R^{13}$ are optionally substituted with one or more, the same or different, $R^{15}$;
$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;
$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and
$R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethyl amino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$R^{20}$ and $R^{30}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{20}$ and $R^{30}$ are optionally substituted with one or more, the same or different, $R^{40}$;
$R^{40}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{40}$ is optionally substituted with one or more, the same or different, $R^{41}$; and
$R^{41}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n are each individually and independently 1, 2, or 3.

In certain embodiments, $R^{10}$ and $R^{11}$ and the attached atoms come together to form a heterocyclyl optionally substituted with one or more, the same or different, $R^{15}$.

In certain embodiments, $R^{12}$ and $R^{13}$ and the attached atoms come together to form a heterocyclyl optionally substituted with one or more, the same or different, $R^{15}$.

In certain embodiments, the disclosure relates to compounds Formula IV:

Formula IV

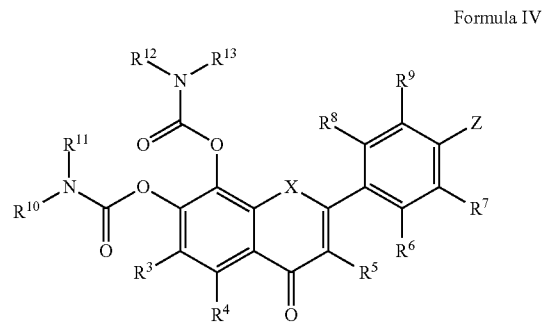

or salts thereof wherein
X is O, S, or NH;
Z is hydrogen, amino, diaminoalkyl, or heterocyclyl such as pyrrolidinyl optionally substituted with one or more, the same or different, $R^{15}$;
$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;
$R^{10}$, $R^{11}$, $R^{12}$, and $R^{13}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$, $R^{11}$, $R^{12}$, and $R^{13}$ are optionally substituted with one or more, the same or different, $R^{15}$; or
$R^{12}$ and $R^{11}$ and the attached atoms come together to form a heterocyclyl optionally substituted with one or more, the same or different, $R^{15}$;
$R^{12}$ and $R^{13}$ and the attached atoms come together to form a heterocyclyl optionally substituted with one or more, the same or different, $R^{15}$;
$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds Formula V:

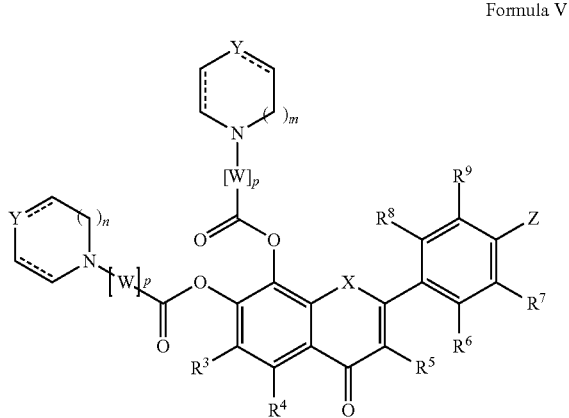

Formula V or salts thereof wherein
the broken lines are optionally double bonds;
n is 0, 1, or 2;
m is 0, 1, or 2;
p is 0, or 11 to 22;
W is at each occurrence $CH_2$, $CHR^{14}$, $CR^{14}_2$, C=O, O, S, NH, or $NR^{14}$;
X is O, S, or NH;
Y is at each occurrence selected from O, S, $CH_2$, CH, $CHR^{14}$, C=O, NH, or $NR^{14}$;
Z is hydrogen, amino, diaminoalkyl, or heterocyclyl such as pyrrolidinyl optionally substituted with one or more, the same or different, $R^{15}$;
$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, $(alkyl)_2$amino, alkylsulfinyl, alkyl sulfonyl, aryl sulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;
$R^{14}$ is alkyl, halogen, nitro, cyano, hydroxy, amino, mercapto, formyl, carboxy, carbamoyl, alkoxy, alkylthio, alkylamino, $(alkyl)_2$amino, alkylsulfinyl, alkyl sulfonyl, arylsulfonyl, carbocyclyl, aryl, or heterocyclyl, wherein $R^{14}$ is optionally substituted with one or more, the same or different, $R^{15}$;
$R^{15}$ is independently selected alkyl, halogen, nitro, cyano, hydroxy, amino, mercapto, formyl, carboxy, carbamoyl, alkoxy, alkylthio, alkylamino, $(alkyl)_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 0 or 1.
In certain embodiments, m is 0 or 1.
In certain embodiments, p is 0, 1, or 2.
In certain embodiments, W is a bond when p is 0 or $CH_2$ when p is 1 or 2.
In certain embodiments, X is O.
In certain embodiments, Y is NH or $NR^{14}$.
In certain embodiments, Z is H.
In certain embodiments, the disclosure relates to compounds Formula VI:

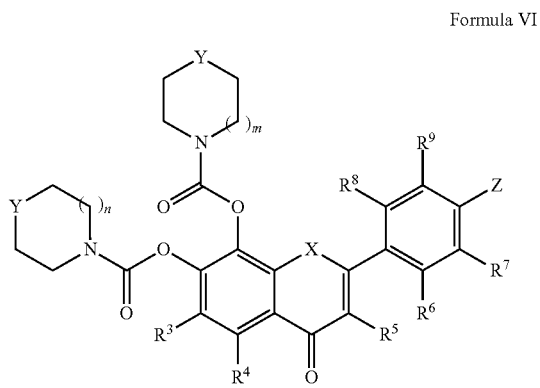

Formula VI or salts thereof wherein
n is 0, 1, or 2;
m is 0, 1, or 2;
X is O, S, or NH;
Y is at each occurrence selected from O, S, $CH_2$, $CHR^{14}$, C=O, NH, or $NR^{14}$;
Z is hydrogen, amino, diaminoalkyl, or heterocyclyl such as pyrrolidinyl optionally substituted with one or more, the same or different, $R^{15}$;
$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, $(alkyl)_2$amino, alkylsulfinyl, alkyl sulfonyl, aryl sulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;
$R^{14}$ is alkyl, halogen, nitro, cyano, hydroxy, amino, mercapto, formyl, carboxy, carbamoyl, alkoxy, alkylthio, alkylamino, $(alkyl)_2$amino, alkylsulfinyl, alkyl sulfonyl, arylsulfonyl, carbocyclyl, aryl, or heterocyclyl, wherein $R^{14}$ is optionally substituted with one or more, the same or different, $R^{15}$;
$R^{15}$ is independently selected alkyl, halogen, nitro, cyano, hydroxy, amino, mercapto, formyl, carboxy, carbamoyl, alkoxy, alkylthio, alkylamino, $(alkyl)_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 0 or 1.
In certain embodiments, m is 0 or 1.
In certain embodiments, X is O.
In certain embodiments, Y is NH or $NR^{14}$.
In certain embodiments, Z is H.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No.

6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glyceryl behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the inhibitor(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more inhibitors. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered in combination with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methyl salicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

Methods of Use

In certain embodiments, the disclosure relates to methods of preventing or treating a BDNF and TrkB related disease or condition comprising the administering an effective amount of a pharmaceutical composition comprising compounds such as 7,8-dihydroxyflavone, prodrugs, and other compounds disclosed herein, to a subject in need thereof. In some embodiments, the subject is diagnosed with, exhibiting symptoms of, or at risk of the disease or condition. In some embodiments, the disease or condition is depression, anxiety, amytrophic later sclerosis, Alzheimer's disease, Autism spectrum disorders, Huntington's disease, Rett syndrome, epilepsy, Parkinson's disease, post-traumatic stress disorder, dementia, diabetic neuropathy, peripheral neuropathy, obesity, or stroke.

In certain embodiments, the methods described herein include a method of treating or reducing the risk of disorders associated with activation of the TrkB receptor including neurological disorders, neuropsychiatric disorders, and metabolic disorders in a subject. Examples of neurological and neuropsychiatric disorders include depression, anxiety, Alzheimer's, CNS injuries, and the like. Examples of metabolic disorders include obesity and hyperphagia. This method includes the steps of selecting a subject with or at risk of developing the neurological disorder, neuropsychiatric disorder, or obesity, and administering to the subject a therapeutically effective amount of a compound disclosed herein. The compound can be administered systemically (e.g., orally, parenterally (e.g. intravenously), intramuscularly, intreperitoneally, transdermally (e.g., by a patch), extracorporeally, topically, by inhalation, subcutaneously or the like), by administration into the central nervous system (e.g., into the brain (intracerebrally or intra ventricularly), spinal cord, or into the cerebrospinal fluid), or any combination thereof.

The subject in need thereof can be a patient diagnosed as suffering from depression or anxiety. These diseases and their diagnoses are very clearly defined in the "Diagnostic and Statistical Manual of Mental Disorders (DSM-IV)" published by the American Psychiatric Association. This manual sets forth diagnostic criteria, descriptions and other information to guide the classification and diagnosis of mental disorders and is commonly used in the field of neuropsychiatry. In certain embodiments, the patient is being administered an antidepressant or anti-anxiolytic medication. In certain embodiments, the patient has been diagnosed by a mental health professional (e.g., a psychiatrist) with an anxiety or depression disorder. Anxiety can be a symptom of an underlying health issue such as chronic obstructive pulmonary disease (COPD), heart failure, or heart arrhythmia.

The subject in need thereof can be a patient diagnosed as suffering from being overweight or obese. Being overweight and obesity can be diagnosed by health or nutritional professionals (e.g., physicians, nurses, dieticians, and the like) when the patient's body mass index (BMI), a measurement which compares weight and height, is between 25 kg/m and 30 kg/m$^2$, and obese when it is greater than 30 kg/m$^2$.

Also provided is a method of promoting neuroprotection in a subject. This method includes the steps of selecting a subject in need of neuroprotection, and administering to the subject a therapeutically effective amount of a compound disclosed herein. A subject in need of neuroprotection can, for example, be a subject that has amyotrophic lateral sclerosis (ALS) or a central nervous system injury. A central nervous system injury includes, for example, a brain injury, a spinal cord injury, or a cerebrovascular event (e.g., a stroke). Methods can further comprise testing the effectiveness of a compound disclosed herein. Testing the effectiveness can include, but is not limited to, imaging (e.g., Magnetic Resonance Imaging (MM)) and functional measurements (e.g., survival or clinical symptoms like analysis of speech patterns, logic, comprehension, memory, mood, and orientation).

In certain embodiments, the disclosure contemplates the treatment of other mental disorders or conditions by administering effective amounts of compounds disclosed herein. contemplated mental disorders and conditions include, but are not limited to, acute stress disorder, adjustment disorder, adolescent antisocial behavior, adult antisocial behavior, age-related cognitive decline, agoraphobia, alcohol-related disorder, Alzheimer's, amnestic disorder, anorexia nervosa, anxiety, attention deficit disorder, attention deficit hyperactivity disorder, autophagia, bereavement, bibliomania, binge eating disorder, bipolar disorder, body dysmorphic disorder, bulimia nervosa, circadian rhythm sleep disorder, cocaine-addition, dysthymia, exhibitionism, gender identity disorder, Huntington's disease, hypochondria, multiple personality disorder, obsessive-compulsive disorder (OCD), obsessive-compulsive personality disorder (OCPD), posttraumatic stress disorder (PTSD), Rett syndrome, sadomasochism, and stuttering.

Depression

In certain embodiments, the disclosure contemplated the treatment of depression with compounds disclosed herein. The most common psychological conditions is depression. Depression can be divided into several types. Major depression is the most severe form of depression characterized by a severe, persistent depressed mood and loss of interest or pleasure in normal activities accompanied by decreased energy, changes in sleep habits, restless behavior, difficulty concentrating, loss of appetite, feelings of guilt or hopelessness, and in severe cases, psychotic symptoms such as hallucinations, delusions, and even suicidal thoughts. An individual typically has a history (greater than 2 weeks) of persistent sad moods, loss of interest or pleasure in activities once enjoyed, and feelings of guilt or hopelessness, restless behavior, difficulty concentrating, and even suicidal thoughts in order to make a diagnosis of major depression. The Beck's Depression Scale Inventory, or other screen tests for depression, can be helpful in diagnosing depression.

Major depression can be treated with medications and/or counseling. Studies have shown that antidepressant drug therapy combined with psychotherapy appears to have better results than either therapy alone. Medications used include, but are not limited to, tricyclic antidepressants, monoamine oxidase inhibitors, selective serotonin re-uptake inhibitor (SSRIs), and some new antidepressant drugs such as bupropion, reboxetine, trazodone, venlafaxine, and mitrazapine. Antipsychotic medications are needed for patients suffering from more severe forms of psychotic symptoms, such as delusions or hallucinations. Types of psychotherapy that have proven to be particularly effective for treating depression include interpersonal therapy, group therapy, and cognitive behavioral therapy.

Alternative therapeutic methods include the use of herbal products for management of chronic conditions, such as psychiatric disorders, including anxiety and depression. In addition, St. John's Wort (hypericum) has recently gained popularity as an adjunct antidepressant in the United States. The National Institute of Health has recently sponsored a Hypericum Clinical Trial comparing 50 to 150 mg/day of sertraline (Zololoft), 900 to 1800 mg/day of St. John's Wort, and placebo in 300 patients with major depression. The conclusion of the study was St. John's Wort was no more effective for treating major depression of moderate severity than a placebo (NIH News Release, Apr. 9, 2002). Side effects of St. John's Wort are mild and primarily include gastrointestinal symptoms and fatigue. Therefore, there is a need in the art for alternative treatments, which are more effective and are associated with fewer side effects for treating major depression.

A second form of depression is chronic low-grade depression, also known as dysthymia. Dysthymia is present most of the time for a period of two or more years wherein an individual experiences a decrease in his/her overall level of energy, appetite, and sleep, as well as has feelings of low self-esteem and hopelessness. These symptoms cause distress and the individual has difficulty functioning in everyday activities. These symptoms, however, are not as severe as those symptoms experienced in major depression. The cause and maintenance of these symptoms are often due to one of the following problems: loss of a friend, substantial disappointment at work or home, prolonged or chronic illness, and alcohol or drug abuse. People who suffer from dysthymia are at an increased risk for episodes of major depression. This produces a behavioral pattern called "double depression" wherein the individual is mildly depressed most of the time, with periodic symptoms of major depression.

The least severe form of depression is a depressed mood. This is an emotional state dominated by feelings of sadness, gloominess, or emptiness, which may be associated with lack of energy. Depressed moods are usually temporary responses to an unhappy or stressful event. Treatments for such conditions are the same as discussed above in treatments for mild depressive disorders.

Autism Spectrum Disorders

In certain embodiments, the disclosure contemplated the treatment of autism spectrum disorders with compounds disclosed herein. Autism Spectrum Disorder, including Asperger Syndrome, is a spectrum of neurodevelopmental disorders characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities.

Administration of compounds disclosed herein may be when a child or infant shows the early signs of signs of autism spectrum disorder or other abnormal social or behavioral development, or about the time of developmental landmarks in infants or children that show early signs of autism spectrum disorder or other abnormal or behavioral development. A therapeutic intervention administered during this period could reset the developmental trajectory of the child preventing the acquisition of second order social impairments.

Bipolar Disorders

In certain embodiments, the disclosure contemplated the treatment of bipolar disorders with compounds disclosed herein. Bipolar disorder affects men and women equally and typically appears between the ages of 15 and 25. As opposed to unipolar major depression, the incidence of bipolar disorder does not vary widely around the world. The exact cause is unknown, but it is linked to areas of the brain which regulate mood, and has a strong genetic component. The American Psychiatric Association's "Diagnostic and Statistical Manual of Mental Disorders" describes two types of bipolar disorder, type I and type II. The type I (formerly known as manic depressive disorder), there has been at least one full manic episode. People with this type, however, may also experience episodes of major depression. In type II disorder, periods of "hypomania" involve more attenuate (less severe) manic symptoms that alternate with at least one major depressive episode. When the patients have an acute exacerbation, they may be in a manic state, depressed state, or mixed state. The manic phase is characterized by elevated mood, hyperactivity, over-involvement in activities, inflated self-esteem, a tendency to be easily distracted, or little need for sleep. In the depressive phase, there is loss of self-esteem, withdrawal, sadness, or a risk of suicide. Either the manic or the depressive episodes can predominate and produce a few mood swings, or the patterns of the mood swing may be cyclic. While in either phase, patients may abuse alcohol or other substances, which worsens the symptoms.

Methods for treating bipolar disorders differ depending upon the state of the patient. During an acute phase, hospitalization may be required to control the symptoms. In order to reduce the risk of switching into mania, hypomania or rapid cycling, a combination of a mood stabilizer (e.g. lithium; valproate) and/or antidepressants (e.g., bupropion) is utilized for controlling bipolar disorders. Even though lithium is often utilized in controlling manic and depressive relapses, careful medical supervision along with maintaining salt intake, avoiding non-steroidal anti-inflammatory drugs, and undertaking weight-reduction diets are typically performed in order to reduce possible renal failure. Valproate also is characterized by severe side effects including nausea, vomiting, anorexia, heartburn, and diarrhea. Finally, the use of antidepressants for suppressing bipolar disorder is typically monitored in order to achieve symptomatic remission. Therefore, safer therapeutic methods are needed in the art in order to reduce the severe side effects associated with current treatments of bipolar disorders.

In certain embodiments, the disclosure contemplated the treatment of cyclothymic disorders with compounds disclosed herein. Cyclothymic disorders are similar to bipolar disorders, but less extreme. Cyclothymic disorders are characterized by stages of mild mood changes with stages of mild depression and excitement (hypomania). The changes in mood are very irregular and abrupt, but the severity of the swings is less. Cyclothymia is treated like bipolar disorders, though often not as aggressively. Thus, safer treatments are needed in the art.

Anxiety Disorders

In certain embodiments, the disclosure contemplated the treatment of anxiety disorders with compounds disclosed herein. Anxiety disorders, panic attacks, and agoraphobia are conditions that occur as a manifestation of primary mood disorders such as depression. Anxiety is a feeling of apprehension or fear that lingers due to an individual's perception of persistent and unrelenting stress. Anxiety is typically accompanied by various physical symptoms including twitching, trembling, muscle tension, headaches, sweating (e.g., night sweats), dry mouth, or difficulty swallowing. Some people also report dizziness, a rapid or irregular heart rate, increased rate of respiration, diarrhea, or frequent need to urinate when they are anxious. Fatigue, irritable mood, sleeping difficulties, decreased concentration, sexual problems, or nightmares are also common. Some people are more sensitive to stress and are thus more likely to develop anxiety disorders. The propensity to succumb to anxiety attacks may be due to genetic predisposition or by previous (e.g. childhood) exposure to certain stresses.

Treatment of anxiety disorders includes diagnostic tests for blood differential and thyroid function as well as an electrocardiogram (EKG). If any worrisome physical signs or symptoms do not accompany the anxiety, a referral to a mental health care professional is recommended. Psychotherapy such as cognitive-behavior therapy (CBT) along with the medication benzodiazepines, which facilitate the actions of gamma-aminobutyric acid (GABA), the major inhibitory neurotransmitter in the nervous system, are the most effective in severe cases of anxiety. In addition to these treatments, use of antidepressants such as imipramine and the selective serotonin re-uptake inhibitor (SSRI) paroxetine have been shown to produce antianxiety benefit to anxiety patients. Treatment with benzodiazepines, however, is accompanied by fatigue, drowsiness, and unsteadiness. After successive treatments with benzodiazepines, patients often develop dependence to the drug and, therefore, careful medical monitoring is required. Thus, there is a need in the art for treatments that provide less drug dependence along with a reduction in side effects and costs.

In certain embodiments, the disclosure contemplated the treatment of panic disorders with compounds disclosed herein. Panic disorder, one of the anxiety disorders, is characterized by repeated and unexpected attacks of intense fear and anxiety. Panic attacks are usually not related to a particular situation and typically "peak" within ten minutes of their onset. The exact cause of panic disorder is unknown, but it is associated with multiple physiological factors. Panic disorder can occur with or without agoraphobia, but agoraphobia develops in one-third of cases.

In certain embodiments, the disclosure contemplated the treatment of agoraphobia with compounds disclosed herein. Agoraphobia is a disorder characterized by avoidance of crowds, and open and public places, particularly if escape or assistance is not immediately available. The development of agoraphobia may involve learned behavior, since it reflects a fear of experiencing panic attacks in unprotected settings, and sometimes the association of panic attacks with areas where they have occurred. Panic disorder can occur in children, but the average age of onset is 25 years old. Panic disorder affects middle-aged and older adults as well. Studies have shown that women are 2 to 3 times more likely to be affected.

Symptoms of panic disorder include shortness of breath, dizziness, palpitations, trembling, sweating, choking, nausea, numbness, chest pain, hot flashes or chills, fear of dying, fear of losing control, or fear of going insane. Symptoms of agoraphobia include anxiety about being in places where escape might be difficult, fear of being alone, fear of losing control in a public place, feeling of helplessness, or feelings of detachment. Treatments for both disorders are similar to treatment of anxiety. Antidepressant medicines are typically used for treatment of many people with panic disorder and agoraphobia including SSRIs such as Paxil. Behavior therapies are also used in conjunction with drug therapy including relaxation techniques, pleasant mental imagery, and cognitive behavioral therapy to restructure distorted and harmful interpretations of particular situations.

Attention Deficit Disorder (ADD)

In certain embodiments, the disclosure contemplated the treatment of attention deficit disorders (ADD) with compounds disclosed herein. Symptoms include developmentally inappropriate levels of attention, concentration, activity, distractibility, and impulsivity. There are three subcategories of attention deficit disorder: (1) attention deficit/hyperactivity disorder of the combined type; (2) attention deficit/hyperactivity disorder of the predominantly inattentive type; and (3) attention deficit/hyperactivity disorder of the predominantly hyperactive or impulsive type.

A typical treatment strategy for ADD is using psychotropic medications such as Dexedine (dextroamphetamine), Ritalin (methylphenidate), and Cylert (magnesium pemoline). Antidepressants (such as amitriptyline or fluoxetine), tranquilizers (such as thionidazine), alpha-adrenergic agonist (clonidine), and caffeine have also been tried to treat ADD. The disadvantage of these drugs is the lack of long term information on the affect these drugs have on the cognitive and emotional development of ADD children. In addition, medications such as antidepressants, tranquilizers, and caffeine have met with little success. A significant amount of research has been carried out studying psychological therapeutic treatments such as contingency management (e.g. time out), cognitive-behavioral treatment (e.g. self-monitoring, verbal self-instruction, problem solving strategies, and self-reinforcement), parent counseling, and individual psychotherapy. Studies using these techniques have yielded mixed results and no studies have been carried out combining psychological interventions with stimulant medications. Therefore, parents are directed to manage the symptoms and direct the child's energy to constructive and educational paths.

Sleep Disorders

In certain embodiments, the disclosure contemplated the treatment of sleep disorders with compounds disclosed herein. A sleep disorder is a disruptive pattern of sleep that may include difficulty: falling or staying asleep, falling asleep at inappropriate times, excessive total sleep time, or abnormal behaviors associated with sleep. There are more than 100 different disorders of sleeping and waking. They can be grouped into four main categories: problems with staying and falling asleep (insomnia, e.g.), problems with staying awake (sleep state misperception, e.g.), problems with adhering to a regular sleep schedule (hypersomnias such as narcolepsy, e.g.), and sleep disruptive behaviors (sleep walking, e.g.). Both insomnia and sleep disruptive behaviors could be direct results of a patient suffering from a psychological disorder such as depression or anxiety.

In certain embodiments, the disclosure contemplated the treatment of insomnia with compounds disclosed herein. Insomnia includes any combination of difficulty with falling asleep, staying asleep, intermittent wakefulness, and early-morning awakening and can lead to the following disorders: psychophysiological, delayed sleep phase syndrome, hypnotic dependent disorder, and stimulant dependent sleep disorder. Episodes may be either transient (2-3 weeks) or chronic. Common factors associated with insomnia are depression, anxiety, stress, illness, caffeine, abuse of alcohol, medication, illness, physical discomfort, and counterproductive sleep habits such as early bedtimes and daytime napping. Treatment of insomnia is related to the cause. If there is an obvious physical or psychological cause (such as depression), it is the first focus, of treatment.

Sleep disruptive behaviors include sleep terror disorder, sleep walking or REM behavior disorders (a type of psychosis related to lack of REM sleep and lack of dreaming). Symptoms of sleep disruptive behaviors are depressed mood, anxiety, apathy, difficulty concentrating, irritability, daytime fatigue, drowsiness, and difficulty falling asleep. Again, treatment of sleep disruptive behaviors is often related to the cause. If there is an obvious physical or psychological cause, it is the first focus of treatment.

Posttraumatic Stress Disorder (PTSD)

In one aspect of the present disclosure, the psychiatric disorder to be treated is PTSD. PTSD is defined by DSM-IV as an anxiety disorder that an individual may develop following exposure to a traumatic event, and is characterized by (1) re-experiencing the traumatic event, such as recurrent nightmares, intrusive recollections of the event, flashbacks, physiological and psychological responses to internal or external cues relating to the event, etc; (2) persistent avoidance of thoughts, people or places associated with the event; (3) numbing of general responsiveness such as emotional detachment, restricted affect or loss of interest in activities; and (4) persistence of increased arousal such as exaggerated startle response, hypervigilance, irritability, or difficulty sleeping, etc. In the US the lifetime prevalence of PTSD is at least 1%, and in high-risk populations, such as combat veterans or victims of criminal violence, prevalence is reported to be between 3 and 58%; PTSD is therefore of considerable public health concern.

Schizophrenia

In certain embodiments, the disclosure contemplated the treatment of schizophrenia with compounds disclosed herein. Schizophrenia is characterized by a breakdown of thought processes and by poor emotional responsiveness and is generally accompanied by social or occupational dysfunction. It is often described in terms of positive and negative symptoms. Positive symptoms can include delusions, disorganized speech and thinking, and tactile, auditory, visual, olfactory, and gustatory hallucinations, typically regarded as manifestations of psychosis. Positive symptoms generally respond well to medication. Negative symptoms are deficits of normal emotional responses or of other thought processes, and respond less well to medication. They commonly include flat or blunted affect and emotion, poverty of speech, inability to experience pleasure, lack of desire to form relationships, and lack of motivation. Research suggests that negative symptoms contribute more to poor quality of life, functional disability, and the burden on others than do positive symptoms. Individuals with prominent negative symptoms often have a history of poor adjustment before the onset of illness, and response to medication is often limited.

The onset of schizophrenia symptoms typically occurs in young adulthood. Diagnosis typically involves the patient meeting three criteria. The first is characteristic symptoms, in which the patient experiences two or more symptoms for more than one month including delusions, hallucinations, disorganized speech, catatonic behavior, and negative symptoms. The second is social or occupational dysfunction. The third is a significant duration, generally about six months. Treatment is generally anti-psychotic medications, often in combination with psychological and social supports.

A subject undergoing treatment with the methods of the disclosure may exhibits an improvement in one or more symptoms associated with the psychiatric disorder. For a description of the relevant symptoms, see, for example, the DSM-IV ((1994) Diagnostic and Statistical Manual of Mental Disorders (4th ed., American Psychiatric Association, Washington, D.C.)), which is herein incorporated by reference. The efficacy of the methods of the disclosure can be assessed using any clinically recognized assessment method for measuring a reduction of one or more symptoms of the particular psychiatric disorder. Examples of such assessment methods are described in, for example, in Experiment 7 of PCT Application WO02/078629. "Alleviation of symptoms," in the context of a behavioral disorder, refers to improvement in the social or psychological function or health of a patient, as evaluated by any measure accepted in the art. Preferably, "alleviation of symptoms" is a clinically recognizable decrease in symptoms described in DSM-IV-TR (American Psychiatric Association, 2000). The psychosocial function of a patient may be evaluated using standard measures provided in DSM-IV-TR (American Psychiatric Association, 2001), such as the Global Assessment of Functioning Scale and the Social and Occupational Functioning Assessment Scale.

EXAMPLES

Substituted flavone derivatives were prepared (See FIG. 1) in purity of >95%, by $^1$H NMR, HPLC (HPLC, 254 nm). The synthetic route is illustrated in the schemes below. Starting materials were typically purchased from commercial sources.

Procedure for Preparation
4-oxo-2-phenyl-4H-chromene-7,8-diyl diacetate

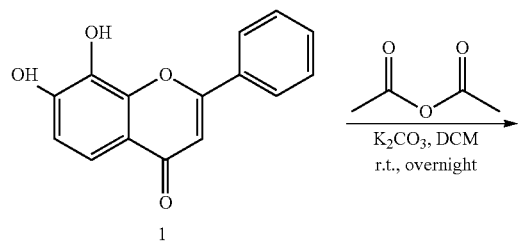

Compound 1 (100 mg, 0.4 mmol) was added to a suspension of $K_2CO_3$ (342 mg, 2.5 mmol) and acetic anhydride (0.1 mL, 0.8 mmol) in DCM. After stirring at r.t. overnight, the mixture was filtered and evaporated under reduced pressure. The residue was washed by ethyl ether to afford the product as a white solid (71 mg, yield: 53.3%). $^1$H NMR (400 MHz, $CD_3OD$): δ ppm 8.06 (d, J=8.8 Hz, 1H), 7.93-7.95 (m, 2H), 7.58-7.61 (m, 3H), 7.38 (d, J=8.4 Hz, 1H), 6.93 (s, 1H), 2.48 (s, 3H), 2.37 (s, 3H). Purity: 99.8% (254 nm); MS: 339.0 $[M+1]^+$ Preparation of
4-oxo-2-phenyl-4H-chromene-7,8-diyl
bis(2,2-dimethylpropanoate) compound $R_5$

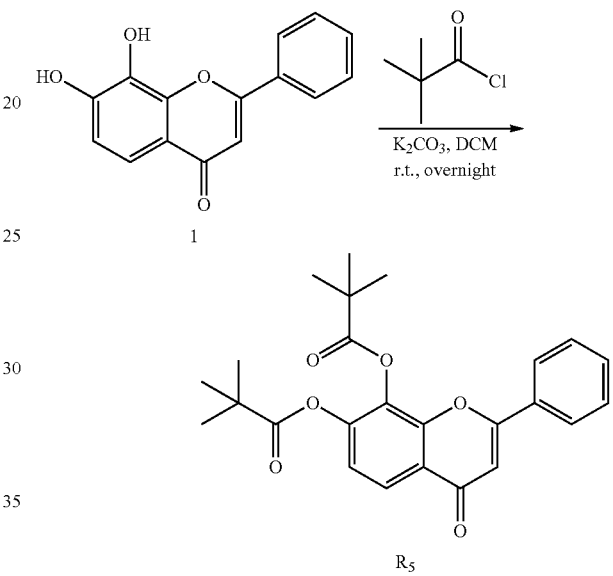

Compound 1 (150 mg, 0.6 mmol) was added to a suspension of $K_2CO_3$ (341 mg, 2.48 mmol) and pivaloyl chloride (0.2 mL, 1.2 mmol) in DCM. After stirring at r.t. overnight, the mixture was filtered and evaporated under reduced pressure. The residue was washed by ethyl ether to afford the product as a red solid (52 mg, yield: 20.9%). $^1$H NMR (400 MHz, $CDCl_3$): δ ppm 8.12 (d, J=8.8 Hz, 1H), 7.80-7.82 (m, 2H), 7.50-7.55 (m, 3H), 7.20 (d, J=8.4 Hz, 1H), 6.76 (s, 1H), 1.45 (s, 9H), 1.35 (s, 9H). Purity: 99.6% (254 nm); MS: 445.1 $[M+1]^+$ Preparation of
4-oxo-2-phenyl-4H-chromene-7,8-diyl
bis(3-methylbutanoate) compound $R_{12}$

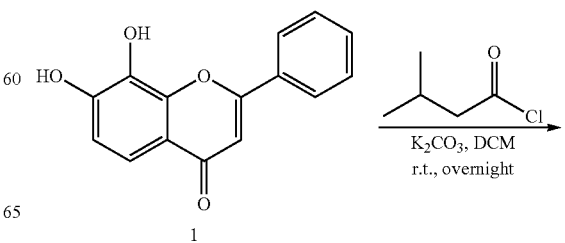

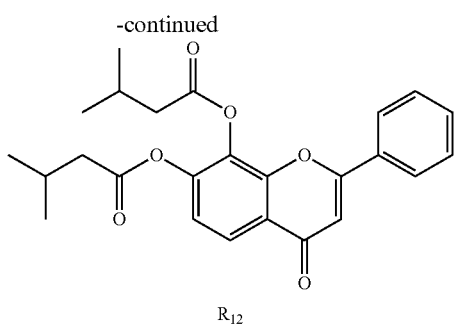

R₁₂

Compound 1 (150 mg, 0.6 mmol) was added to a suspension of K₂CO₃ (341 mg, 2.48 mmol) and isovaleryl chloride (0.2 mL, 1.2 mmol) in DCM. After stirring at r.t. overnight, the mixture was filtered and evaporated under reduced pressure. The residue was washed by ethyl ether to afford the product as a white solid (57 mg, yield: 23.1%). $^1$H NMR (400 MHz, CDCl₃): δ ppm 8.12 (d, J=8.8 Hz, 1H), 7.80-7.82 (m, 2H), 7.48-7.55 (m, 3H), 7.23-7.26 (m, 1H), 6.78 (s, 1H), 2.59 (d, J=6.8 Hz, 2H), 2.49 (d, J=6.8 Hz, 2H), 2.24-2.32 (m, 2H), 1.09-1.11 (m, 12H). Purity: 99.6% (254 nm); MS: 445.0 [M+1]⁺

Preparation of
4-oxo-2-phenyl-4H-chromene-7,8-diyl
bis(dimethylcarbamate) compound R₇

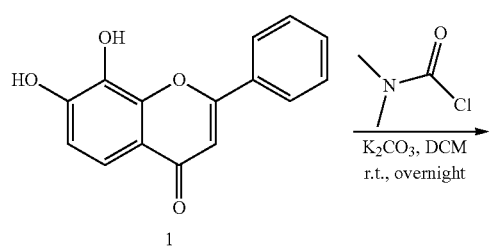

Compound 1 (200 mg, 0.8 mmol) was added to a suspension of K₂CO₃ (458 mg, 3.3 mmol) and dimethylcarbamoyl chloride (0.3 mL, 1.7 mmol) in DCM. After stirring at r.t. overnight, the mixture was filtered and evaporated under reduced pressure. The residue was washed by ethyl ether to afford the product as a white solid (53 mg, yield: 15.9%, Lot#: MC0777-38-1). $^1$H NMR (400 MHz, CDCl₃): δ ppm 8.07 (d, J=8.8 Hz, 1H), 7.82-7.84 (m, 2H), 7.49-7.54 (m, 3H), 7.32-7.34 (m, 1H), 6.79 (s, 1H), 3.24 (s, 3H), 3.15 (s, 3H), 3.11 (s, 3H), 3.05 (s, 3H). Purity: 98.2% (254 nm); MS: 397.0[M+1]⁺

Preparation of
4-oxo-2-phenyl-4H-chromene-7,8-diyl dipropionate
compound R₄

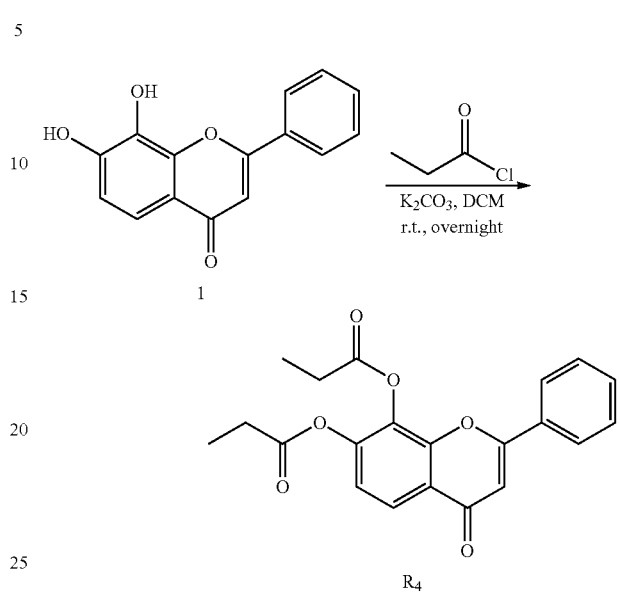

Compound 1 (200 mg, 0.8 mmol) was added to a suspension of K₂CO₃ (458 mg, 3.3 mmol) and propionyl chloride (0.3 mL, 1.7 mmol) in DCM. After stiring at r.t. overnight, the mixture was filtered and evaporated under reduced pressure. The residue was washed by ethyl ether to afford the product as a yellow solid (51 mg, yield: 17.4%). $^1$H NMR (400 MHz, CDCl₃): δ ppm 8.13 (d, J=8.8 Hz, 1H), 7.79-7.81 (m, 2H), 7.51-7.55 (m, 3H), 7.25-7.27 (m, 1H), 6.79 (s, 1H), 2.75 (q, J=7.6 Hz, 2H), 2.65 (q, J=7.6 Hz, 2H), 1.38 (t, J=7.6 Hz, 3H), 1.31 (t, J=7.6 Hz, 3H). Purity: 95.5% (254 nm); MS: 367.0 [M+1]⁺

Preparation of diethyl
(4-oxo-2-phenyl-4H-chromene-7,8-diyl) dicarbonate
compound R₃

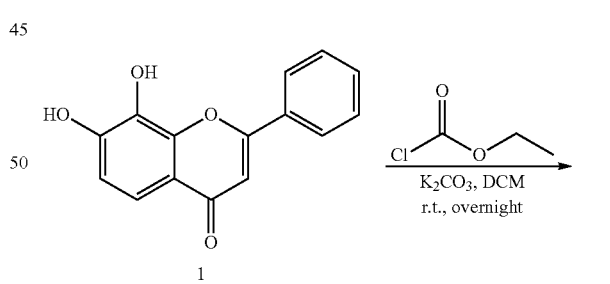

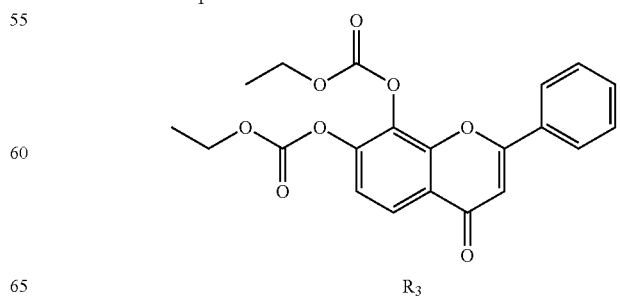

R₃

Compound 1 (200 mg, 0.8 mmol) was added to a suspension of K₂CO₃ (458 mg, 3.3 mmol) and ethyl chloroformate (0.3 mL, 1.7 mmol) in DCM. After stirring at r.t. overnight, the mixture was filtered and evaporated under reduced pressure. The residue was washed by ethyl ether to afford the product as a white solid (50 mg, yield: 15.9%). ¹H NMR (400 MHz, CDCl₃): δ ppm 8.14 (d, J=8.8 Hz, 1H), 7.85-7.87 (m, 2H), 7.50-7.56 (m, 3H), 7.35-7.38 (m, 1H), 6.83 (s, 1H), 4.35-4.43 (m, 4H), 1.41-1.44 (m, 6H). Purity: 96.0% (254 nm); MS: 399.0 [M+1]⁺

Preparation of
4-oxo-2-phenyl-4H-chromene-7,8-diyl
bis(ethylcarbamate) compound R₆

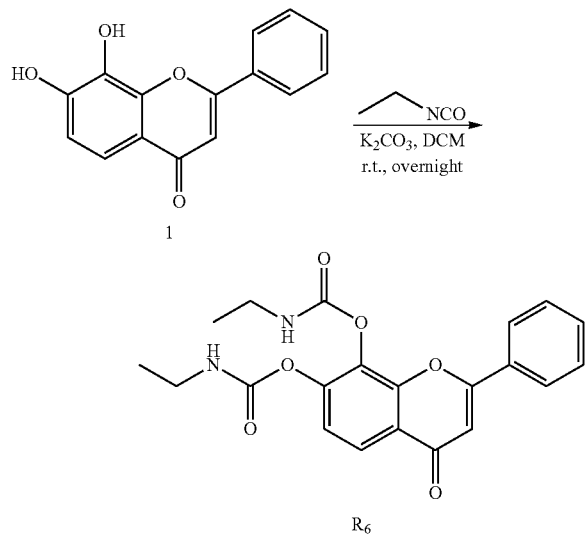

Compound 1 (200 mg, 0.8 mmol) was added to a suspension of K₂CO₃ (458 mg, 3.3 mmol) and ethyl isocyanate (0.3 mL, 1.7 mmol) in DCM. After stirring at r.t. overnight, the mixture was filtered and evaporated under reduced pressure. The residue was washed by ethyl ether to afford the product as a white solid (70 mg, yield: 22.5%). ¹H NMR (400 MHz, CDCl₃): δ ppm 8.05 (d, J=8.8 Hz, 1H), 7.84-7.86 (m, 2H), 7.47-7.53 (m, 3H), 7.28-7.30 (m, 1H), 6.79 (s, 1H), 5.45-5.46 (m, 1H), 5.22-5.23 (m, 1H), 3.32-3.54 (m, 4H), 1.23-1.30 (m, 6H). Purity: 99.8% (254 nm); MS: 397.1 [M+1]⁺

Preparation of
4-oxo-2-phenyl-4H-chromene-7,8-diyl
diisonicotinate compound R₁₁

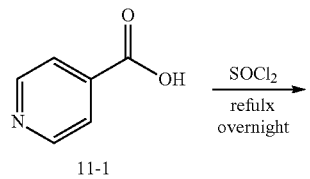

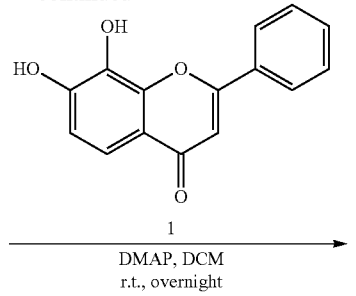

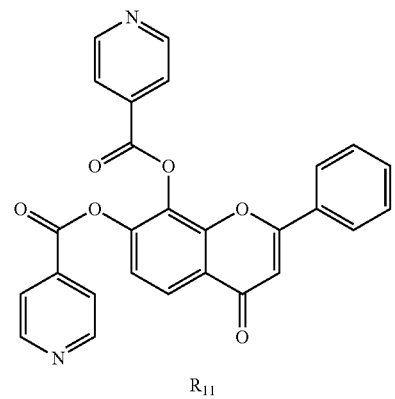

A solution of compound 11-1 (600 mg, 4.9 mmol) in SOCl₂ (20 mL) was refluxed overnight under Ar atmosphere. Then the resulting mixture was evaporated under reduced pressure to remove the SOCl₂, the residue was used for the next step directly without further purification.

Compound 1 (200 mg, 0.8 mmol) was added to a solution of DMAP (1.2 g, 4.8 mmol) and Compound 11-2 (690 mg, 4.9 mmol) in DCM (5 mL), and the mixture was stirred at r.t. overnight. The mixture was filtered and evaporated under reduced pressure. The residue was washed by ethyl ether to afford the product as a white solid (80 mg, yield: 21.9%). The product was confirmed by HPLC, LCMS and ¹H NMR. ¹H NMR (400 MHz, CDCl₃): δ ppm 8.89 (d, J=6.0 Hz, 2H), 8.83 (d, J=6.0 Hz, 2H), 8.28 (d, J=8.8 Hz, 1H), 7.99-8.00 (m, 2H), 7.91-7.92 (m, 2H), 7.67-7.69 (m, 2H), 7.46-7.48 (m, 2H), 7.36-7.40 (m, 2H), 6.86 (s, 1H). Purity: 93.7% (254 nm); MS: 465.0 [M+1]⁺

Preparation of Amino Acid Esters

Figure 2:
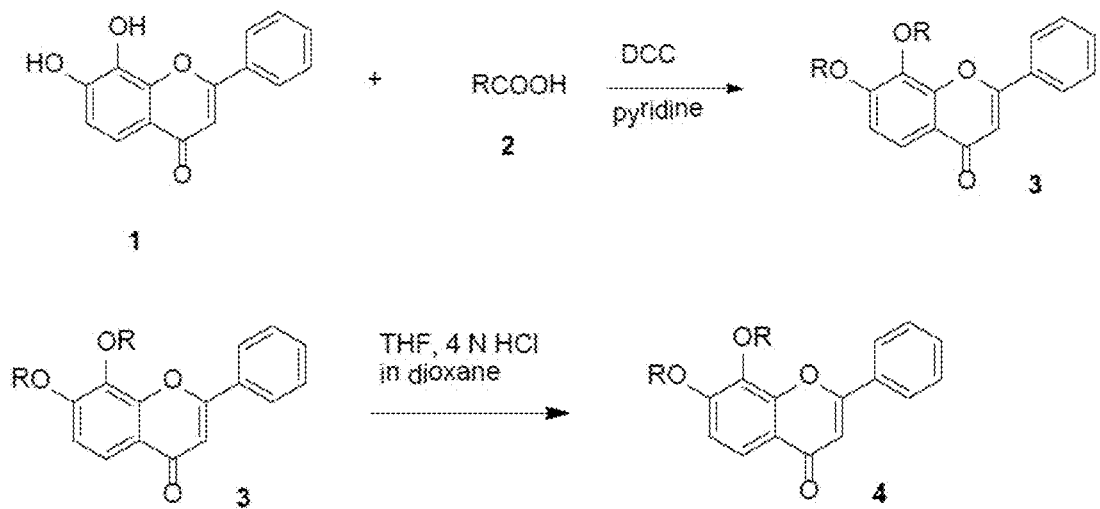
FIG. 2 schematically illustrates a method of preparing embodiments of this disclosure.
Figure 3:
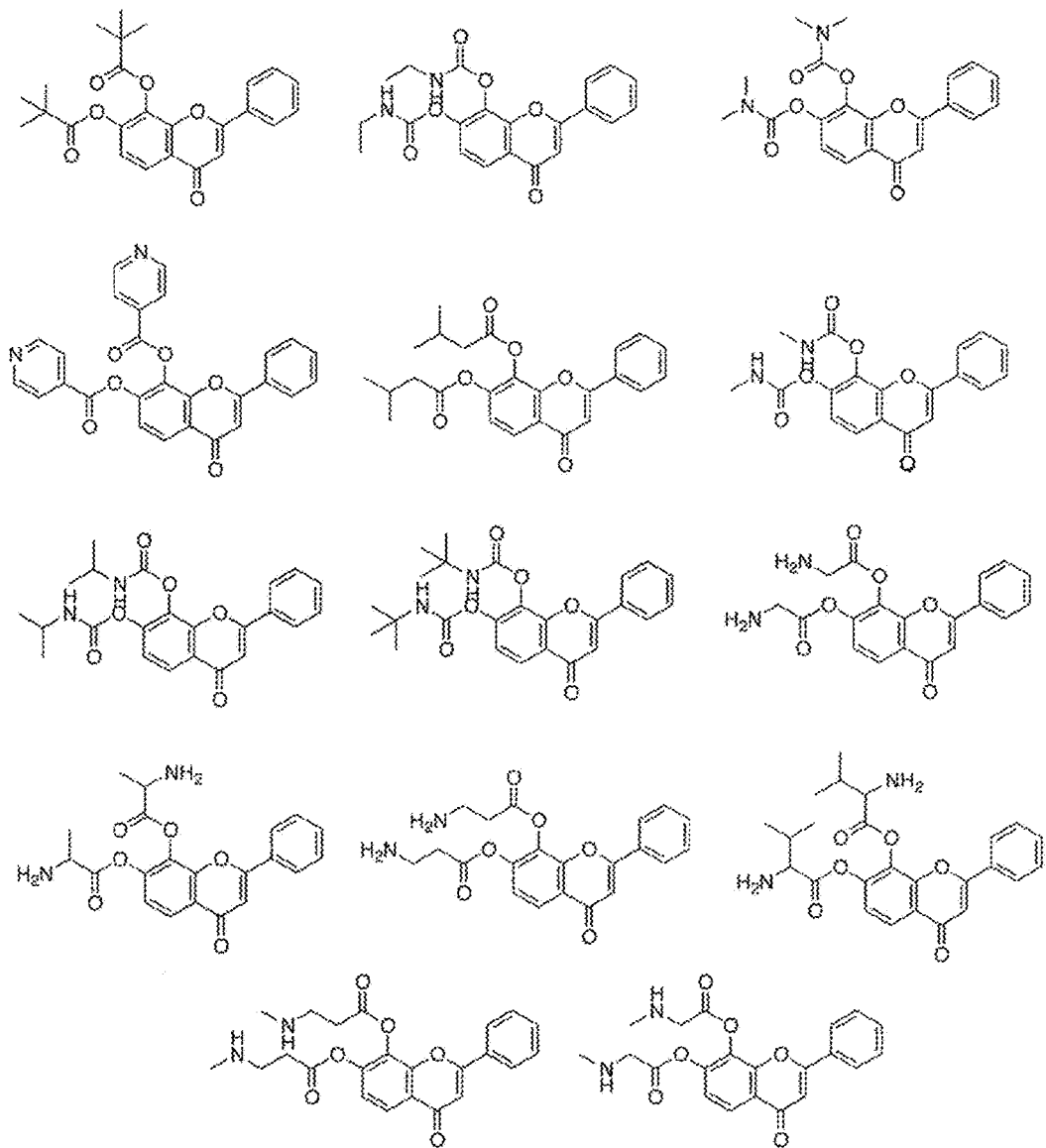
FIG. 3 illustrates various embodiments of the disclosure.

FIG. 2 illustrates the preparation of certain amino acid derivatives. To a solution of 2 mmol of 7,8-dihydroxyflavone (1) in 10 ml of anhydrous pyridine was added 4 mmol of 2. After cooling in an ice bath, DCC (4 mmol) was added and stirring was continued for 24 hours. Dichloromethane was added and the insoluble byproducts were filtered off. The filtrate was concentrated by rotary evaporation at below 35° C. and was then evaporated twice from toluene to remove any residual pyridine. Purification by flash silica gel chormatography with hexane/EtOAc (65/35) provided 3 as a white foam or solid.

To a solution of 0.5 mmol 3 in 10 ml of THF was added 10 ml of 4 N HCl in dioxane. After stirring overnight, 40 ml of ether was added and the solid was collected by vacuum filtration to provide 4 as the di or mono HCl salt.
2a: R=N-Bocglycine
2b: R=N-Boc-L-alanine
2c: R=N-Boc-L-valine
2d: R=N-Boc-sarcosine 2e: R=N-Boc-b-Alanine
2f: R=N-Boc-N-methyl-b-Alanine
3a: R=N-Bocglycine (25% yield)
3b: R=N-Boc-L-alanine (60% yield)
3c: R=N-Boc-L-valine (44% yield)
3d: R=N-Boc-sarcosine (30% yield)
3e: R=N-Boc-b-Alanine (80% yield)
3f: R=N-Boc-N-methyl-b-Alanine (35% yield)
4a: R=Glycine (89% yield)
4b: R=L-Alanine (90% yield)
4c: R=L-Valine (66% yield)
4d: R=Sarcosine (92% yield)
4e: R=b-Alanine (93% yield)
4f: R=N-methyl-b-Alanine (96% yield)
Compound Prepared by a Same or Similar Method as Provided Above 4-Oxo-2-phenyl-4H-chromene-7,8-diyl-bis(2-aminoacetate) dihydrochloride $^1$H NMR (300 MHz, D$_2$O) δ7.95 (d, 1H), 7.74 (d, 2H), 7.74 (m, 5H), 6.81 (s, 1H), 4.79 (s, 15H), 4.45 (d, 2H), 4.34 (d, 2H), 3.70 (s, 1H). LC 90%; MS: calculated: 368.34; found: 396.1 (M+1). Elemental Analysis: calculated C: 49.69, found C: 49.62; MS: calculated H: 4.39, found H: 4.45, LC: calculated N6.10, found: 6.10, calculated Cl: 15.44, found Cl: 15.36.

(2S, 2'S)-4-Oxo-2-phenyl-4H-chromene-7,8-diyl-bis(2-aminopropanoate) dihydrochloride $^1$H NMR (300 MHz, D$_2$O) δ7.94 (d, 1H), 7.71 (d, 2H), 7.46 (m, 4H), 6.78 (s, 1H), 4.77 (m, 2H), 1.83 (d, 3H), 1.76 (d, 3H), 1.45 (m, 1H). LC: 0.13 alanine. MS: calculated: 396.36, found: 397.1 (M+1). Elemental Analysis: calculated C: 52.73, found C: 52.83; MS: calculated H: 4.85, found H: 4.79, LC: calculated N5.86, found: 5.82, calculated Cl: 14.82, found Cl: 14.90.

4-Oxo-2-phenyl-4H-chromene-7,8-diyl-bis(3-aminopropanoate) dihydrochloride $^1$H NMR (300 MHz, D$_2$O) δ7.73 (d, 1H), 7.71 (m, 2H), 7.50 (m, 3H), 7.40 (d, 1H), 6.81 (s, 1H), 4.83 (m, H), 3.39 (m, 4H), 3.374 (d, 2H), 3.37 (m, 2H). LC: 100%. MS: calculated: 396.36, found: 397.1 (M+1). Elemental Analysis: calculated C: 52.73, found C: 52.55; MS: calculated H: 4.85, found H: 4.80, LC: calculated N5.86, found: 5.92, calculated Cl: 14.82, found Cl: 14.99.

(2S, 2'S)-4-Oxo-2-phenyl-4H-chromene-7,8-diyl-bis(2-amino-3-methylbutanoate) Dihydrochloride $^1$H NMR (300 MHz, D$_2$O) δ7.88 (d, 1H), 7.58 (m, 3H), 7.41 (m, 3H), 6.68 (s, 1H), 4.77 (s, H), 4.49 (d, 1H), 4.44 (d, 1H), 2.65 (m, 2H), 1.19 (m, 9H), 1.06 (m, 4H). LC: 0.15 eq. valine. MS: calculated: 452.5, found: 453.2 (M+1). Elemental Analysis: calculated C: 55.07, found C: 54.87; MS: calculated H: 5.95, found H: 45.82, LC: calculated N5.14, found: 5.22, calculated Cl: 13.00, found Cl: 13.08.

4-Oxo-2-phenyl-4H-chromene-7,8-diyl-bis(3-methylaminopropanoate) dihydrochloride $^1$H NMR (300 MHz, D$_2$O) δ67.94 (d, 1H), 7.70 (d, 2H), 7.47 (m, 3H), 7.39 (d, 1H), 6.80 (s, 1H), 4.83 (m, H), 3.43 (m, 4H), 3.28 (d, 2H), 3.21 (m, 2H), 2.77 (s, 3H), 2.72 (s, 3H). LC: 100%. MS: calculated: 424.45, found: 425.2 (Parent+1). Elemental Analysis: calculated C: 52.85, found C: 53.09; MS: calculated H: 5.44, found H: 5.18, LC: calculated N5.36, found: 5.30, calculated Cl: 14.92, found Cl: 14.96.

4-Oxo-2-phenyl-4H-chromene-7,8-diyl-bis(2-(methylamino)acetate) Dihydrochloride $^1$H NMR (300 MHz, D$_2$O) δ7.94 (d, 1H), 7.75 (d, 2H), 7.48 (m, 5H), 6.80 (s, 1H), 4.80 (m, H), 4.55 (s, 2H), 4.53 (d, 2H), 2.93 (d, 7H). LC: 90%. MS: calculated: 396.36, found: fragmented. NMR: Elemental Analysis: calculated C: 53.74, found C: 53.58; calculated H: 4.72, found H: 4.69, LC: calculated N5.97, found: 5.90, calculated Cl: 15.11, found Cl: 15.02.

4-oxo-2-phenyl-4H-chromene-7,8-diyl bis(piperazine-1-carboxylate) and 4-oxo-2-phenyl-4H-chromene-7,8-diyl bis(4-methylpiperazine-1-carboxylate)

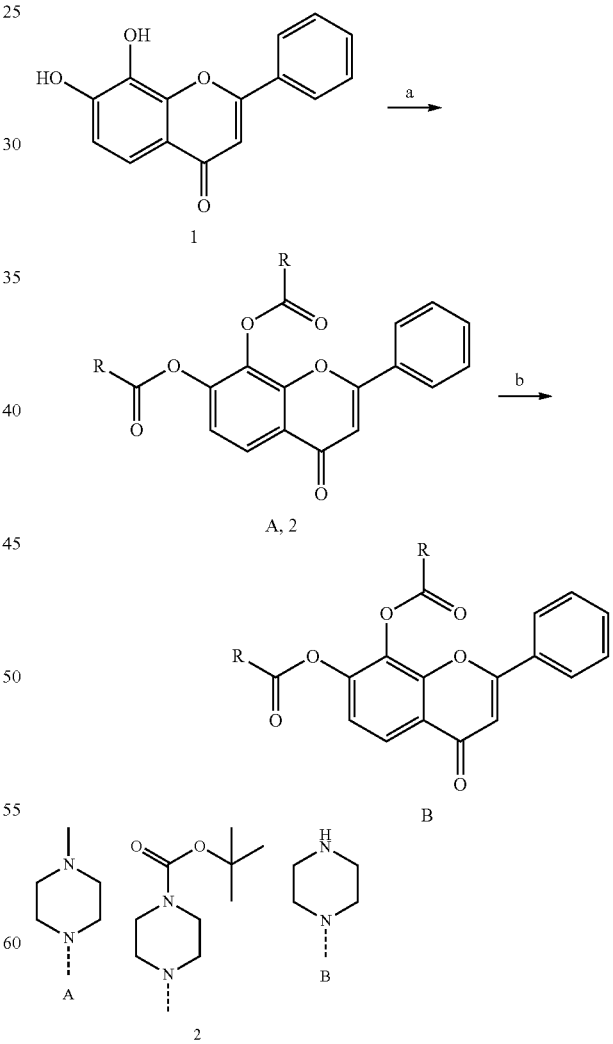

Compound A—4-oxo-2-phenyl-4H-chromene-7,8-diylbis (4-methylpiperazine-1-carboxylate). To a solution of 1-methylpiperazine (3.9 g, 39.2 mmol) in dry THF (100 mL) was added triphosgene (3.9 g, 13.1 mmol) at −78° C. The mixture was stirred at −78° C. for 1 h, then warmed to 0° C. The solvent was removed under vacummn, then acetone (100 mL), water (10 mL) and pyridine (10 mL) were added to the residue. The mixture was cooled to 0° C. again and compound 1 (1.0 g, 3.9 mmol) was added. The reaction mixture was stirred at room temperature overnight. The mixture was concentrated and water (100 mL) was added, then extracted with EtOAc (100 mL×3). The combined organic layer was washed with brine, dried over $Na_2SO_4$, concentrated, and the residue was purified by column chromatography on silica gel (eluent: petroleum ether/ethyl acetate=2/1) to give compound A (0.40 g, yield 20.2%) as a light yellow solid. $^1$H NMR (300 MHz, $CDCl_3$): (ppm) 8.08 (d, J=9.0 Hz, 1H), 7.84 (d, J=6.3 Hz, 2H), 7.53-7.49 (m, 3H), 7.30 (d, J=9.0 Hz, 1H), 6.79 (s, 1H), 3.85-3.58 (m, 8H), 2.53-2.45 (m, 8H), 2.39 (s, 3H), 2.36 (s, 3H); >98% at 214 nm, MS (ESI) m/z=507.2 [M+H]$^+$.

Compound 2. Procedure was the same as above to give 0.81 g as a white solid (30.4% yield). $^1$H NMR (300 MHz, $CDCl_3$): (ppm) 8.10 (d, J=8.7 Hz, 1H), 7.81 (d, J=8.1 Hz, 2H), 7.52-7.45 (m, 3H), 7.31 (d, J=9.0 Hz, 1H), 6.79 (s, 1H), 3.78-3.45 (m, 16H), 1.51 (s, 9H), 1.49 (s, 9H).

Compound B—4-oxo-2-phenyl-4H-chromene-7,8-diylbis (piperazine-1-carboxylate) dihydrochloride. To a solution of compound 2 (0.5 g, 0.74 mmol) in dioxane (5 mL) was added 2 M HCl/dioxane (5 mL). The mixture was stirred at room temperature for 2 h. The precipitate was collected by filtration and then washed with MeOH and $Et_2O$ to give compound B (270.0 mg, yield 48.5%, 2 eq. HCl salt) as a white solid. $^1$H NMR (300 MHz, DMSO-$d_6$): (ppm) 9.78-9.45 (br, 4H), 7.99-7.95 (m, 3H), 7.67-7.63 (m, 3H), 7.51 (d, J=8.7 Hz, 1H), 7.11 (s, 1H), 4.05-3.70 (m, 8H), 3.27-3.14 (m, 8H); >98% at 214 nm, MS (ESI) m/z=479.1 [M+H]$^+$.

Metabolism Studies

Metabolism studies indicate that the catechol group is conjugated by glucuronidation, sulfation and methylation in liver, which leads to the poor oral bioavailability upon oral administration. A PK study in C57BL6 mice shows that 7,8-DHF exhibits approximately 5% oral bioavailability. Most of 7,8-DHF is conjugated and metabolized within 30 min. Derivatives with various moieties on the catechol group in 7,8-DHF were synthesized. These derivatives were monitored for intestine microsomal stability, liver microsomal stability and plasma stability. In addition, compounds with favorable chemical stability and Caco-2 permeability were examined.

Figure 4:
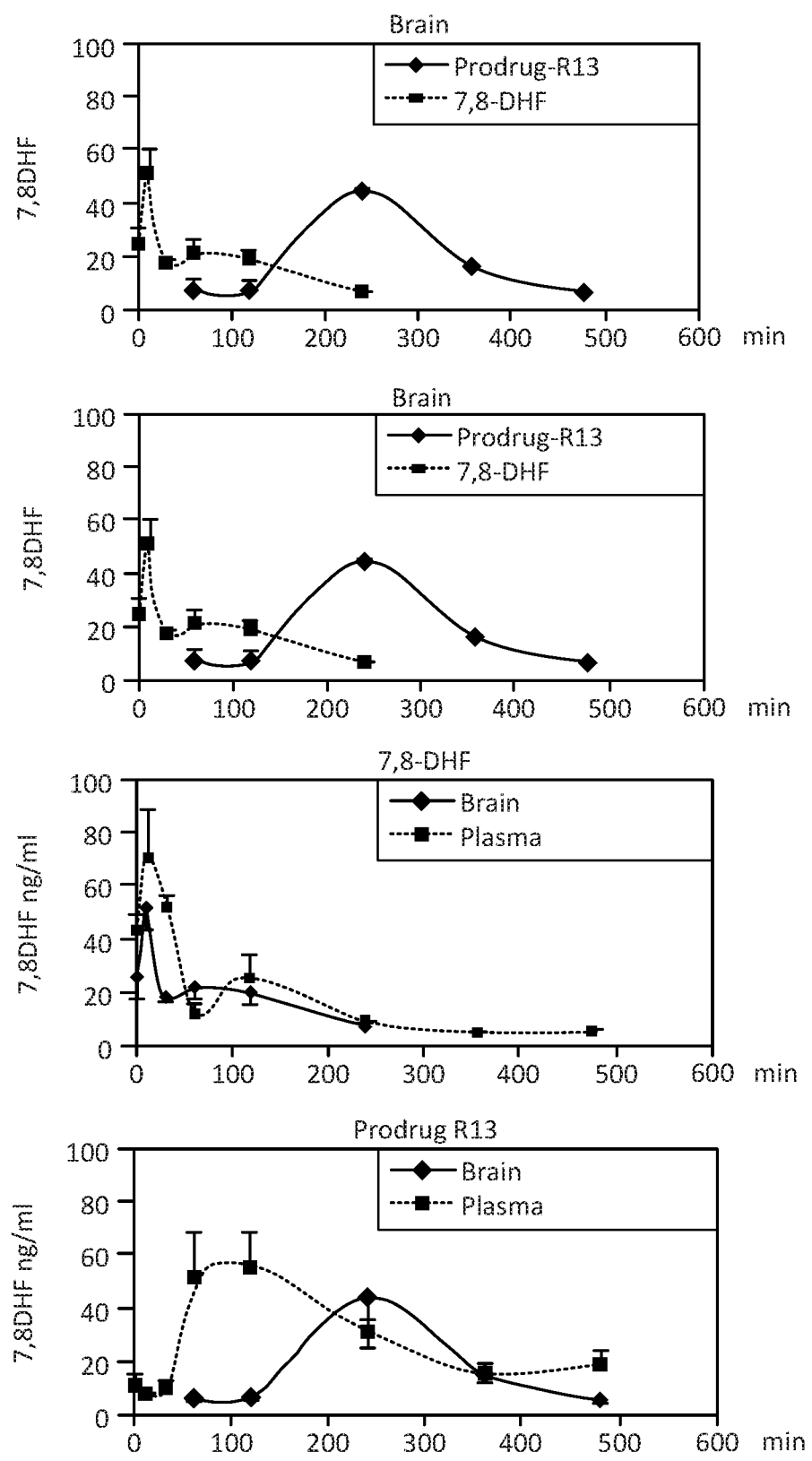
FIG. 4 show data indicating $R_{13}$ improves 7,8-DHF oral bioavailability and brain concentrations. Top, brain 7,8-DHF concentration after oral administration of parent compound or $R_{13}$ prodrug. Middle and bottom, 7,8-DHF plasma and brain concentrations comparison after oral administration of parent compound or $R_{13}$.
Figure 5:
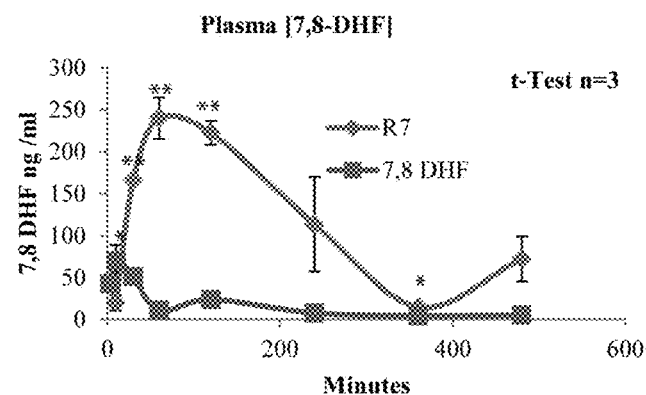
FIG. 5 shows data indicating plasma 7,8-DHF concentration after administering R$_7$ is higher than parent 7,8-DHF via oral administration. Two months old mice were orally administrated 78 mg/kg of the R$_7$, and mice were sacrificed at different time points (n=3), the plasma was then harvested and analyzed by HPLC/MS. The ratio of AUC$_{last}$ of R7 versus parent drug is 7.2 folds.
Figure 6:
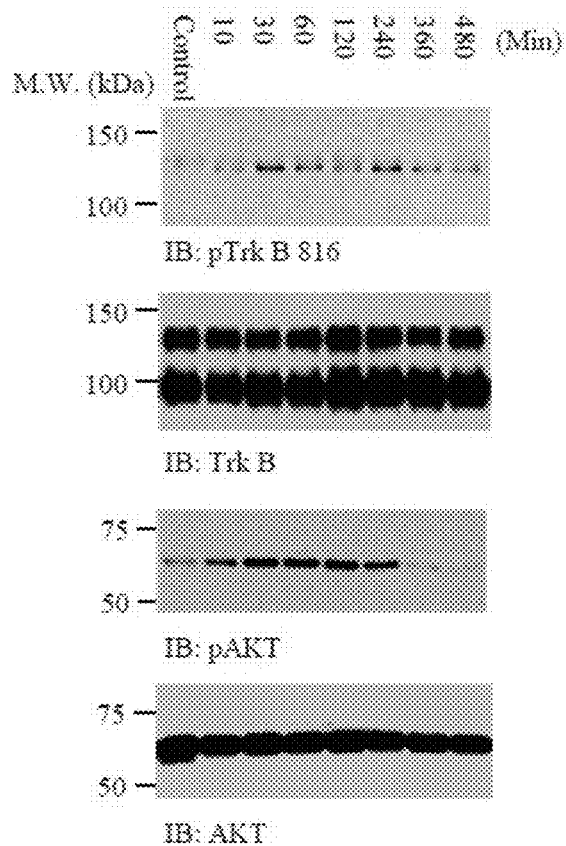
FIG. 6 shows data indicate that R7 administration triggers TrkB activation and its downstream Akt signaling activation in mouse brain. R7 (78 mg/kg equal to about 50 mg/kg of 7,8-DHF) was administered orally. The mice were sacrificed at different intervals. The brain lysates were analyzed by immunobotting with various antibodies including p-TrkB 816, Total TrkB, p-Akt and total Akt.

Notably, R7 is stable in both pH 1.2 and 7.4 buffer, indicating that this derivative has desirable chemical stability. R7 and R13 were chosen to analyze their in vivo PK profiles. The concentration of 7,8-DHF's in brain was examined at different time points after oral administrated 72.5 mg/kg, which is the molecular equivalent of 50 mg/kg of 7,8-DHF. In plasma, 7,8-DHF peaked at around 100 min for R13, whereas administration of the parent compound 7,8-DHF, occurred at 10 min. The oral bioavailability of R13 was around 10%. Prodrug R13 significantly elongated 7,8-DHF brain availability and the maximal concentrations took place at 4 h, while parent 7,8-DHF was not detectable after 4 h (FIG. 4).

Carbmate R7 was tested. R7 displays approximately 35% oral bioavailability. 7,8-DHF plasma concentrations from R7 (78 mg/kg about 50 mg/kg parent compound dosage) are higher than parent compound, 7,8-DHF (50 mg/kg P.O.) upon oral administration. 7,8-DHF was detectable in the plasma at 8 h, indicating the prodrug can sustainably release 7,8-DHF in the circulation system. Accordingly, it half-life t ½ is about 195 min with Tmax=60 min. The Cmax plasma [7,8-DHF] for parent (7,8-DHF) is 70 ng/ml, whereas R7 is 262 ng/ml. The ratio of R7/parent compound of $AUC_{last}$ is 46949/6500=7.2.

The TrkB signaling in mouse brains was monitored from the in vivo PK study. Immunoblotting analysis demonstrates that TrkB and its downstream p-Akt signalings were potently activated upon oral administration of R7, tightly correlating with 7,8-DHF concentrations in plasma. The pharmacodynamic (PD) study fits well with the in vivo PK data, underscoring that the released 7,8-DHF from R7 triggers the long-lasting TrkB signalings in mouse brain.

The invention claimed is:

1. A method of treating a BDNF and TrkB related disease or condition comprising administering an effective amount of a pharmaceutical composition to a subject in need thereof, wherein the pharmaceutical composition comprises a compound of Formula I:

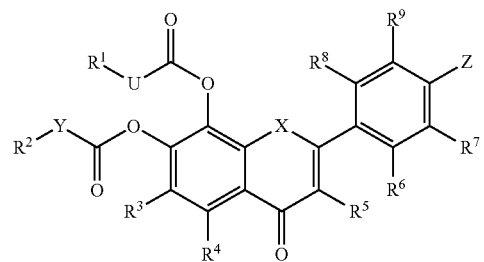

Formula I or a salt thereof, wherein:

X is O, S, or NH;

U and Y are each O, S, NH, Nalkyl, or $CH_2$;

Z is hydrogen, amino, diaminoalkyl, or heterocyclyl optionally substituted with one or more, the same or different, $R^{15}$;

$R^1$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, arylsulfonyl, carbocyclyl, or aryl, wherein $R^1$ is optionally substituted with one or more, the same or different, $R^{15}$;

$R^2$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^2$ is optionally substituted with one or more, the same or different, $R^{15}$;

$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$ amino, alkylsulfinyl, alkylsulfonyl, arylsulfonyl, carbocyclyl, or aryl, wherein $R^{15}$ is optionally substituted with one or more, the same or different, $R^{16}$; and R¹⁶ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and a pharmaceutically acceptable excipient, wherein the disease or condition is depression, schizophrenia, obsessive-compulsive disorder, anorexia nervosa, bulimia nervosa, anxiety, amyotrophic lateral sclerosis, Autism spectrum disorders, post-traumatic stress disorder, Alzheimer's disease, Huntington's disease, Rett syndrome, epilepsy, Parkinson's disease, dementia, diabetic neuropathy, peripheral neuropathy, or stroke.

2. The method of claim 1, wherein the subject is diagnosed with, exhibiting symptoms of, or at risk of the disease or condition.

3. The method of claim 1, wherein the disease is depression and the pharmaceutical composition is administered in combination with an anti-depressant.

4. The method of claim 3, wherein the anti-depressant is a selective serotonin reuptake inhibitor, a serotonin-norepinephrine reuptake inhibitor, a noradrenergic and specific serotonergic antidepressant, a norepinephrine reuptake inhibitor, a norepinephrine-dopamine reuptake inhibitor, a selective serotonin reuptake enhancer, a norepinephrine-dopamine disinhibitor, a tricyclic antidepressant, or a monoamine oxidase inhibitor.

5. The method of claim 1, wherein U and Y are NH or Nalkyl.

6. The method of claim 1, wherein U and Y are oxygen.

7. The method of claim 1, wherein R¹ and R² are alkyl.

8. The method of claim 1, wherein the compound is selected from:

4-oxo-2-phenyl-4H-chromene-7,8-diyl bis(methylcarbamate);

4-oxo-2-phenyl-4H-chromene-7,8-diyl dipropionate;

diethyl (4-oxo-2-phenyl-4H-chromene-7,8-diyl) dicarbonate;

4-oxo-2-phenyl-4H-chromene-7,8-diyl bis(ethylcarbamate);

4-oxo-2-phenyl-4H-chromene-7,8-diyl bis(dimethylcarbamate); and 4-oxo-2-phenyl-4H-chromene-7,8-diyl bis(3-methylbutanoate), or a salt thereof.

9. The method of claim 1, wherein the disease or condition is Alzheimer's disease.

10. The method of claim 1, wherein the disease or condition is Parkinson's disease.

11. The method of claim 1, wherein the disease or condition is depression.

12. The method of claim 1, wherein the disease or condition is Huntington's disease.

13. The method of claim 3, wherein the anti-depressant is citalopram, escitalopram, fluoxetine, fluvoxamine, paroxetine, sertraline, vilazodone, desvenlafaxine, duloxetine, milnacipran, venlafaxine, mianserin, mirtazapine, atomoxetine, mazindol, reboxetine, viloxazine, bupropion, tianeptine, aminopine, agomelatine, amitriptyline, clomipramine, doxepin, imipramine, trimipramine, desipramine, nortriptyline, protriptyline, isocarboxazid, moclobemide, phenelzine, selegiline, or tranylcypromine.

14. A method of treating a BDNF and TrkB related disease or condition comprising administering an effective amount of a pharmaceutical composition to a subject in need thereof, wherein the pharmaceutical composition comprises 4-oxo-2-phenyl-4H-chromene-7,8-diyl bis(2,2-dimethylpropanoate) and a pharmaceutically acceptable excipient, wherein the disease or condition is depression, schizophrenia, obsessive-compulsive disorder, anorexia nervosa, bulimia nervosa, anxiety, amyotrophic lateral sclerosis, autism spectrum disorders, post-traumatic stress disorder, Alzheimer's disease, Huntington's disease, Rett syndrome, epilepsy, Parkinson's disease, dementia, diabetic neuropathy, peripheral neuropathy, or stroke.

* * * * *